United States Patent [19]

Nappa et al.

[11] Patent Number: 6,093,859
[45] Date of Patent: *Jul. 25, 2000

[54] PROCESS FOR THE MANUFACTURE OF 1,1,1,3,3-PENTAFLUOROPROPANE

[75] Inventors: Mario Joseph Nappa, Newark; V. N. Mallikarjuna Rao, Wilmington, both of Del.; Allen Capron Sievert, Elkton, Md.

[73] Assignee: E. I. du Pont de Nemours and Company, Wilmington, Del.

[ * ] Notice: This patent is subject to a terminal disclaimer.

[21] Appl. No.: 09/323,736

[22] Filed: Jun. 1, 1999

Related U.S. Application Data

[63] Continuation of application No. 09/005,400, Jan. 9, 1998, Pat. No. 5,945,573
[60] Provisional application No. 60/036,328, Jan. 31, 1997.

[51] Int. Cl.[7] ............................. C07C 19/08; C07C 17/25
[52] U.S. Cl. ..................... 570/175; 570/176; 570/156; 570/157; 570/158
[58] Field of Search .................................. 570/175, 176, 570/156, 157, 158

[56] References Cited

U.S. PATENT DOCUMENTS

| | | |
|---|---|---|
| 2,599,631 | 6/1952 | Harmon . |
| 2,942,036 | 6/1960 | Smith . |
| 3,636,172 | 1/1972 | Gardner . |
| 4,828,818 | 5/1989 | Carlson et al. . |
| 5,136,113 | 8/1992 | Rao . |
| 5,396,000 | 3/1995 | Nappa et al. . |
| 5,414,165 | 5/1995 | Nappa et al. . |
| 5,856,593 | 1/1999 | Powell et al. . |

FOREIGN PATENT DOCUMENTS

| | | |
|---|---|---|
| 0 514 932 A2 | 11/1992 | European Pat. Off. . |
| 0 406 748 B1 | 9/1994 | European Pat. Off. . |
| 0 703 207 A1 | 3/1996 | European Pat. Off. . |
| 0 726 243 A1 | 8/1996 | European Pat. Off. . |
| 2 710 054 | 3/1995 | France . |
| 9-67281 | 3/1997 | Japan . |
| 9-95459 | 4/1997 | Japan . |
| WO 93/02150 | 2/1993 | WIPO . |
| WO 96/05157 | 2/1996 | WIPO . |

OTHER PUBLICATIONS

Derwent Abstract (Week 9720) re JP 09 067 281 A, (1997).
Derwent Abstract (Week 9724) re JP 09 095 459 A, (1997).

*Primary Examiner*—A Siegel

[57] ABSTRACT

A process is disclosed for producing the hydrofluorocarbon $CF_3CH=CF_2$. The process involves dehydrofluorinating $CF_3CH_2CF_3$ at an elevated temperature in the vapor phase over a catalyst of (1) aluminum fluoride, (2) fluorided alumina, (3) metal supported on a trivalent aluminum compound containing fluoride anion, (4) lanthanum fluoride, (5) fluorided lanthanum oxide, (6) metal supported on a trivalent lanthanum compound containing fluoride anion, (7) trivalent chromium compounds and/or (8) catalysts of (a) at least one compound selected from the oxides, fluorides and oxyfluorides of magnesium, zinc and mixtures of magnesium and zinc, and optionally (b) at least one compound selected from the oxides, fluorides and oxyfluorides of aluminum, provided that the atomic ratio of aluminum to the total of magnesium and zinc in said catalyst is about 1:4, or less, to produce a product containing $CF_3CH=CF_2$ and HF. The $CF_3CH=CF_2$ may then be reacted in the vapor phase with hydrogen over a hydrogenation catalyst in the presence of HF to produce $CF_3CH_2CHF_2$.

15 Claims, No Drawings

PROCESS FOR THE MANUFACTURE OF 1,1,1,3,3-PENTAFLUOROPROPANE

This application is a continuation of U.S. patent application Ser. No. 09/005,400, filed Jan. 9, 1998 now U.S. Pat. No. 5,945,573 and claims the priority benefit of U.S. Provisional Application Ser. No. 60/036,328 filed Jan. 31, 1997.

FIELD OF THE INVENTION

This invention relates to a process for producing fluorine-substituted hydrocarbons, and more particularly to a process for producing 1,1,1,3,3-pentafluoropropane.

BACKGROUND

A number of chlorine-containing halocarbons are considered to be detrimental toward the Earth's ozone layer. There is a world-wide effort to develop materials having lower ozone depletion potential that can serve as effective replacements. For example, the hydrofluorocarbon, 1,1,1,2-tetrafluoroethane (HFC-134a) is being used as a replacement for dichlorodifluoromethane (CFC-12) in refrigeration systems. There is a need for manufacturing processes that provide fluorocarbons that contain less chlorine or no chlorine. The production of hydrofluorocarbons (i.e., compounds containing only carbon, hydrogen and fluorine), has been the subject of considerable interest to provide environmentally desirable products for use as solvents, blowing agents, refrigerants, cleaning agents, aerosol propellants, heat transfer media, dielectrics, fire extinguishants and power cycle working fluids (see, e.g., PCT International Publication No. WO 93/02150).

SUMMARY OF THE INVENTION

A process is provided in accordance with this invention for producing the hydrofluorocarbon $CF_3CH=CF_2$. The process comprises dehydrofluorinating $CF_3CH_2CF_3$ at an elevated temperature in the vapor phase over a catalyst selected from the group consisting of (1) aluminum fluoride, (2) fluorided alumina, (3) metal supported on a trivalent aluminum compound containing fluoride anion (e.g., aluminum fluoride and/or fluorided alumina), (4) lanthanum fluoride, (5) fluorided lanthanum oxide, (6) metal supported on a trivalent lanthanum compound containing fluoride anion (e.g., lanthanum fluoride and/or fluorided lanthanum oxide), (7) trivalent chromium compounds (e.g., $Cr_2O_3$); (8) catalysts of (a) at least one compound selected from the oxides, fluorides and oxyfluorides of magnesium, zinc and mixtures of magnesium and zinc, and optionally (b) at least one compound selected from the oxides, fluorides and oxyfluorides of aluminum, provided that the atomic ratio of aluminum to the total of magnesium and zinc in said catalyst is about 1:4, or less (e.g., 1:9), and mixtures of said catalysts (1) to (8), to produce a product containing $CF_3CH=CF_2$ and HF. The $CF_3CH=CF_2$ may then be reacted in the vapor phase with hydrogen over a hydrogenation catalyst in the presence of HF to produce $CF_3CH_2CHF_2$.

DETAILED DESCRIPTION

This invention provides a process for producing 1,1,1,3,3-pentafluoropropane (i.e., $CF_3CH_2CHF_2$ or HFC-245fa) from 1,1,1,3,3,3-hexafluoropropane (i.e., $CF_3CH_2CF_3$ or HFC-236fa).

In accordance with this invention, $CF_3CH_2CF_3$ is dehydrofluorinated to $CF_3CH=CF_2$ over a selected catalyst.

Suitable catalyst compositions comprising aluminum fluoride and fluorided alumina can be prepared as disclosed in U.S. Pat. No. 5,396,000 which is incorporated in its entirety herein by reference.

Suitable fluorided lanthanum oxide compositions can be prepared in any manner analogous to those known to the art for the preparation of fluorided alumina. For example, the catalyst composition can be prepared by fluorination of lanthanum oxide impregnated with a solution of catalytic metal(s) (e.g., at least one chromium, nickel, manganese, zinc or cobalt compound) which may be in the form of the oxide, oxyhalide, halide, nitrate, sulfate or other compound of the metal. The halides include fluorides, chlorides and bromides.

Suitable catalyst compositions can also be prepared by co-precipitation of the catalytic metal and the lanthanum as the hydroxides which are thereafter dried and calcined to form the mixed oxides, a technique well known to the art. The resulting oxide can then be pretreated as described herein.

Suitable metals for support on trivalent aluminum compounds containing fluoride anion or trivalent lanthanum compounds containing fluoride anion include chromium, magnesium (e.g., magnesium fluoride), Group VIIB metals (e.g., manganese), nickel, cobalt, zinc, and mixtures thereof (e.g., a mixture of chromium and zinc).

The total content of catalytic metal(s) for these compositions (e.g., chromium, nickel, zinc, cobalt and/or magnesium) expressed as metal is typically not more than 50% by weight of the catalyst composition, and is preferably not more than 30% by weight of the catalyst composition; and is usually at least about 0.05% by weight of the catalyst composition, and is preferably at least about 0.1% by weight of the catalyst composition. A particularly preferred range is from 0.1 to 10% by weight of the catalyst composition. Preferably, the catalytic metals are present as halides, oxyhalides including mixed halides and oxyhalides such as metal chlorofluorides, and oxides. The preferred catalytic metals include chromium, nickel, zinc, cobalt and magnesium. Catalysts containing chromium or magnesium are especially preferred.

Catalyst compositions can be fluorinated to the desired fluorine content by treating with a fluorine-containing compound at elevated temperatures, e.g., at about 200° C. to about 450° C. The pretreatment with a vaporizable fluorine-containing compound such as HF, $SF_4$, $CCl_3F$, $CCl_2F_2$, $CHF_3$, $CHClF_2$ or $CCl_2FCClF_2$ can be done in any convenient manner including in the reactor which is to be used for carrying out the dehydrofluorination (and optionally, the hydrogenation reaction). By vaporizable fluorine-containing compound is meant a fluorine-containing compound which, when passed over the catalyst at the indicated conditions, will fluorinate the catalyst to the desired degree.

A suitable catalyst may be prepared, for example, as follows:

A quantity of $La_2O_3$ is impregnated with a solution, usually aqueous, of a catalytically effective amount of one or more of the metal compounds described above (e.g., chromium, cobalt, nickel, zinc and/or magnesium halides). By catalytically effective amount is meant an amount of the metal which causes the production of the desired compounds in the process of the instant invention. Normally, this amount, expressed as metal, will be between about 0.05 to 50 weight percent of the lanthanum oxide support, preferably not more than 30 weight percent, and more preferably 0.1 to 10 weight percent. The impregnated $La_2O_3$ can be dried until essentially all moisture is removed, e.g., for about 18 hours at about 400° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C. and the vaporizable fluorine-containing compound, optionally diluted with an inert gas (e.g., $N_2$) is passed through the reactor. The inert gas can be gradually reduced until only the vaporizable fluorine-containing compound is being passed through the reactor. At this point the temperature can be increased to about 450° C. and held at that temperature to convert the impregnated $La_2O_3$ to a fluorine content corresponding to at least 80% $LaF_3$ by weight, e.g., for 15 to 300 minutes, depending on the flow of the fluorine containing compound and the catalyst volume.

Another suitable procedure for the catalyst preparation is to add ammonium hydroxide to a solution of $La(NO_3)_3.6H_2O$ and, if present, a metal in the form of a water soluble compound, such as zinc nitrate. The ammonium hydroxide is added to the nitrate solution to a pH of about 9.0 to 9.5. At the end of the addition, the solution is filtered, the solid obtained is washed with water, and slowly heated to about 400° C., where it is calcined. The calcined product is then treated with a suitable vaporizable fluorine-containing compound as described above.

Compositions of this invention include catalytic compositions comprising at least one catalytic metal selected from the group consisting of chromium, cobalt, nickel, zinc and magnesium supported on a support of trivalent lanthanum compound containing fluoride anion wherein the weight ratio of the catalytic metal(s) (i.e., total catalytic metal) to lanthanum is from about 1:1 to about 1:999. Of note are compositions where said catalytic metals are supported on lanthanum fluoride; and compositions where said catalytic metals are supported on fluorided lanthanum oxide. Preferably, the total catalytic metal content of these compositions is from about 0.1 to 30 percent by weight, expressed as metal.

Any $Cr_2O_3$ can be used as a catalyst but preferred catalysts include $Cr_2O_3$ prepared by pyrolysis of $(NH_4)_2Cr_2O_7$ and $Cr_2O_3$ having a surface area of about 40 $m^2/g$ or more.

The $Cr_2O_3$ catalyst prepared using the pyrolysis of ammonium dichromate, can be prepared by any method known to the art including those disclosed in U.S. Pat. Nos. 4,843,181 and 5,036,036, which are incorporated herein by reference. The $Cr_2O_3$ obtained in this manner may contain low levels of contaminants (e.g., potassium) which are present as a result of the manufacturing process for the original $(NH_4)_2Cr_2O_7$. The level of potassium or other water-soluble impurities may be reduced by water-washing in a conventional manner.

Other preferred $Cr_2O_3$ catalysts which may be used in the process of this invention include catalysts having a surface area as determined by BET measurement greater than about 100 $m^2/g$, some of which are commercially available. The preparation of such high surface area $Cr_2O_3$ catalysts is described in U.S. Pat. No. 4,828,818 and in European Patent Application Publication No. 514,932.

Other preferred catalysts include catalysts consisting essentially of magnesium fluoride, and catalysts consisting essentially of magnesium fluoride and at least one compound selected from the oxides, fluorides and oxyfluorides of aluminum.

A suitable catalyst may be prepared, for example, as follows:

Magnesium oxide is dried until essentially all water is removed, e.g., for about 18 hours at about 100° C. The dried material is then transferred to the reactor to be used. The temperature is then gradually increased to about 400° C. while maintaining a flow of nitrogen through the reactor to remove any remaining traces of moisture from the magnesium oxide and the reactor. The temperature is then lowered to about 200° C. and a fluoriding agent such as HF or other vaporizable fluorine containing compounds such as $SF_4$, $CCl_3F$, $CCl_2F_2$, $CHF_3$ or $CCl_2FCClF_2$, optionally diluted with an inert gas such as nitrogen is passed through the reactor. The inert diluent can be gradually reduced until only HF or other vaporizable fluorine containing compounds is being passed through the reactor. At this point the temperature can be increased to about 450° C. and held at that temperature to convert the magnesium oxide to a fluoride content corresponding to at least 40% by weight, e.g., for 15 to 300 minutes, depending on the fluoriding agent flowrate and the catalyst volume. The fluorides are in the form of magnesium fluoride or magnesium oxyfluoride; the remainder of the catalyst is magnesium oxide. It is understood in the art that fluoriding conditions such as time and temperature can be adjusted to provide higher than 40 weight % fluoride-containing material.

Another suitable procedure for the catalyst preparation is to add ammonium hydroxide to a solution of magnesium nitrate and if present zinc nitrate and/or aluminum nitrate. The ammonium hydroxide is added to the nitrate solution to a pH of about 9.0 to 9.5. At the end of the addition, the solution is filtered, the solid obtained is washed with water, dried and slowly heated to 500° C., where it is calcined. The calcined product is then treated with a suitable fluorine-containing compound as described above.

Yet another procedure for the preparation of metal (i.e., magnesium optionally containing also zinc and/or aluminum) fluoride catalysts containing one or more metal fluorides is to treat an aqueous solution of the metal(s) halide(s) or nitrate(s) in deionized water with 48% aqueous HF with stirring. Stirring is continued overnight and the slurry evaporated to dryness on a steam bath. The dried solid is then calcined in air at 400° C. for about four hours, cooled to room temperature, crushed and sieved to provide material for use in catalyst evaluations.

The physical shape of the catalyst is not critical and may, for example, include pellets, powders or granules.

The catalytic dehydrofluorination of $CF_3CH_2CF_3$ is suitably conducted at a temperature in the range of from about 300° C. to about 500° C. and preferably from about 375° C. to about 450° C. The contact time is typically from about 1 to about 450 seconds, preferably from about 10 to about 120 seconds..

The effluent from the dehydrofluorination contains $CF_3CH=CF_2$, HF and typically other compounds such as unreacted $CF_3CH_2CF_3$.

In accordance with this invention, $CF_3CH=CF_2$ produced by the catalytic dehydrofluorination of $CF_3CH_2CF_3$ is contacted with hydrogen in the presence of a hydrogenation catalyst and in the presence of HF. $CF_3CH=CF_2$ may be isolated from the dehydrofluorination reaction effluent by conventional techniques such as distillation if desired, and HF may then be separately added in the hydrogenation step. However, it is preferred to pass the HF from the dehydrofluorination, and more preferably the entire effluent from the dehydrofluorination of $CF_3CH_2CF_3$ (including the HF), with hydrogen over the hydrogenation catalyst. While the hydrogenation reaction proceeds even in the absence of HF, the HF present during the hydrogenation step moderates the hydrogenation reaction. In any case, in accordance with this invention, $CF_3CH_2CHF_2$ may be produced from $CF_3CH_2CF_3$ without separation and removal of HF prior to $CF_3CH_2CHF_2$ production. In addition, passing the entire effluent from the dehydrofluorination step onto the hydrogenation step avoids handling concerns associated with olefinic halogenated compounds as well as HF. The HF of the hydrogenation effluent is available for use along with other compounds thereof. For example, the HF is available for azeotropic combination with the fluorinated organic compounds of the effluent from the hydrogenation reaction.

The reaction of $CF_3CH=CF_2$ with hydrogen in the presence of HF employs a hydrogenation catalyst. Normally, the hydrogenation catalyst contains a metal (e.g, a Group VIII metal). The metal may be supported (e.g., Pd supported on alumina, aluminum fluoride, or carbon) or may be unsupported (e.g., Raney nickel). Carbon-supported metal catalysts are preferred, with Pd/C being particularly preferred. The carbon support is preferably washed with acid prior to depositing the metal on it. Procedures for preparing a catalyst of Group VIII metal on an acid-washed carbon support are disclosed in U.S. Pat. No. 5,136,113, the entire contents of which are hereby incorporated herein by reference.

The contact of $CF_3CH=CF_2$ with hydrogen in the presence of a hydrogenation catalyst and HF is suitably conducted at a temperature in the range of from about 50° C. to about 300° C., and preferably from about 50° C. to about 200° C. Contact time is typically from about 5 to 100 seconds, preferably about 10 to 30 seconds.

The molar ratio of hydrogen to $CF_3CH=CF_2$ typically is in the range from about 1:1 to about 50:1, and is preferably from about 1.5:1 to about 25:1, and more preferably from about 2:1 to about 10:1. Normally, at least about 100 ppm HF is present; and typically the HF is approximately stoichiometric with $CF_3CH=CF_2$, especially when the entire effluent from the dehydrofluorination step is passed to the hydrogenation step.

Hydrogen can be fed either in the pure state or diluted with inert gas (e.g., nitrogen, helium or argon).

The reaction products from the hydrogenation may be separated by conventional techniques, such as distillation. $CF_3CH_2CHF_2$ forms an azeotrope with HF; and conventional decantation/distillation may be employed if further purification of $CF_3CH_2CHF_2$ is desired.

The dehydrofluorination step can be beneficially run under reduced pressure (i.e., a pressure less than one atmosphere). The dehydrofluorination can also be beneficially run by co-feeding an inert gas (e.g., nitrogen, helium or argon) while maintaining the total pressure at about atmospheric.

Pressure is not critical for the hydrogenation step. Atmospheric and superatmospheric pressures (e.g., pressure from about 100 kPa to 7000 kPa) are the most convenient and are therefore preferred for hydrogenation.

The hydrogenation and dehydrofluorination reactions may be conducted in any suitable reactor, including fixed and fluidized bed reactors. The reaction vessel should be constructed from materials which are resistant to the corrosive effects of hydrogen fluoride such as Inconel™ or Hastelloy™ nickel alloys.

The $CF_3CH_2CF_3$ used as a reactant in this process may be readily produced by contacting a mixture of hydrogen fluoride and 1,1,1,3,3,3-hexachloropropane (i.e., $CCl_3CH_2CCl_3$ or HCC-230fa) in the vapor phase in the presence of a trivalent chromium catalyst as disclosed in U.S. Pat. No. 5,414,165. The starting material, HCC-230fa, can be prepared by the reaction of carbon tetrachloride with vinylidene chloride as disclosed in Belbachir et al. Makromol. Chem., Vol. 185, 1583–1595 (1984) (see Chemical Abstracts 101:131167).

$CF_3CH_2CHF_2$ has numerous uses including applications in compositions used as refrigerants, blowing agents, propellants, cleaning agents, and heat transfer agents.

Without further elaboration, it is believed that one skilled in the art can, using the description herein, utilize the present invention to its fullest extent. The following specific embodiments are to be construed as illustrative, and not as constraining the remainder of the disclosure in any way whatsoever.

EXAMPLES

Legend:

| 1225zc is $CF_3CH=CF_2$ | 236fa is $CF_3CH_2CF_3$ |
|---|---|
| 245fa is $CF_3CH_2CHF_2$ | 254fb is $CF_3CH_2CH_2F$ |
| CT is contact time | conv. is conversion |
| sel. is selectivity | |

Example 1

$$CF_3CH_2CF_3 \rightarrow (CF_3CH=CF_2 + HF) \rightarrow CF_3CH_2CHF_2$$

A 15 in. (38.1 cm)×⅜ in (0.95 cm) Hastelloy™ nickel alloy tube was filled with 18.2 g (about 13 mL) $Cr_2O_3$ ground to 12/20 mesh (1.68/0.84 mm).

A. Catalyst Activation (1st reactor)

The catalyst was activated as follows: The reactor was heated to 200° C. for two hours while purging with nitrogen (50 sccm, $8.3 \times 10^{-7}$ m³/s). The nitrogen was continued at 50 sccm ($8.3 \times 10^{-7}$ m³/s), and the catalyst contacted with HF (50 sccm, $8.3 \times 10^{-7}$ m³/s) for 15 minutes. The HF flow was raised to 80 sccm ($1.3 \times 10^{-6}$ m³/s) and the nitrogen flow reduced to 20 sccm ($3.3 \times 10^{-7}$ m³/s) for 25 minutes. The temperature was raised to 250° C. for 75 minutes, 300° C. for 75 minutes, 350° C. for 75 minutes, and 400° C. for 75 minutes while maintaining the flows of HF and nitrogen.

B. (Reaction: $CF_3CH_2CF_3 \rightarrow CF_3CH=CF_2 + HF$)

The reactor was heated to 373–398° C. The flow of 1,1,1,3,3,3-hexafluoropropane (6.6 sccm, $1.1 \times 10^{-7}$ m³/s) and nitrogen was begun to the reactor. The effluent of this reactor which contained 1,1,1,3,3-pentafluoropropene (HFC-1225zc) and HF was passed directly into the next reactor.

| Run No. | T ° C. | $N_2$ sccm |
|---|---|---|
| 1 | 373 | 6.5ᵃ |
| 2 | 398 | 6.5 |
| 3 | 398 | 6.5 |
| 4 | 398 | 6.5 |
| 5 | 398 | 0.7ᵇ |

ᵃequivalent to $1.1 \times 10^{-7}$ m³/s
ᵇequivalent to $1.2 \times 10^{-8}$ m³/s C. Hydrogenation of HFC-1225zc One inch (2.54 cm) Monel™ nickel alloy compression fittings were used as a reactor (1.91 cm×6.99 cm internal cavity dimensions). This reactor was filled with 0.5% Pd on acid-washed carbon (4.15 g, 8.5 mL). The reactor was heated to 163° C. and the reactor effluent (including both $CF_3CH=CF_2$ and HF) from B described above (dehydrofluorination of $CF_3CH_2CF_3$) was introduced into the reactor.

| Run No. | CT Sec. | $H_2$ sccm | mole % | | | | % 236fa conv. | % 245fa sel. |
|---|---|---|---|---|---|---|---|---|
| | | | 1225zc | 236fa | 245fa | 254fb | | |
| 1 | 59 | 6.5 | 0.5 | 85.0 | 14.5 | 0.0 | 15.0 | 96.8 |
| 2 | 59 | 6.5 | 1.9 | 77.4 | 20.6 | 0.1 | 22.6 | 91.1 |
| 3 | 60 | 13$^c$ | 0.9 | 77.7 | 21.5 | 0.0 | 22.3 | 96.2 |
| 4 | 60 | 19.5$^d$ | 0.5 | 77.9 | 21.6 | 0.0 | 22.1 | 97.8 |
| 5 | 107 | 19.5 | 0.7 | 79.3 | 20.0 | 0.0 | 20.7 | 96.4 |

$^c$equivalent to $2.2 \times 10^{-7}$ m$^3$/s
$^d$equivalent to $3.2 \times 10^{-7}$ m$^3$/s The contact time shown is the time over the dehydrofluorination catalyst. Run 4, when compared to Run 5, shows that even though the contact time is decreased by the addition of about 10 times the amount of nitrogen as used in Run 5, the conversion is increased.

Example 2

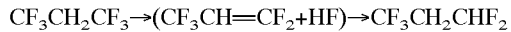

A 15 in (38.1 cm)×⅜ in (0.95 cm) Hastelloy™ nickel alloy tube was filled with 8.48 g (about 13 mL) gamma-alumina ground to 12/20 mesh (1.68/0.84 mm).

A. Catalyst Preparation (1st reactor)

The gamma-alumina catalyst precursor was heated to 200° C. for two hours while purging with nitrogen (50 sccm, $8.3 \times 10^{-7}$ m$^3$/s). The nitrogen was continued at 50 sccm ($8.3 \times 10^{-7}$ m$^3$/s), and the catalyst contacted with HF (50 sccm, $8.3 \times 10^{-7}$ m$^3$/s) for 15 minutes. The HF flow was raised to 80 sccm ($1.3 \times 10^{-6}$ m$^3$/s) and the nitrogen flow reduced to 20 sccm ($3.3 \times 10^{-7}$ m$^3$/s) for 25 minutes. The temperature was raised to 250° C. for 75 minutes, 300° C. for 75 minutes, 350° C. for 75 minutes, and 400° C. for 75 minutes while maintaining the flows of HF and nitrogen to provide a fluorided alumina catalyst.

B. (Reaction: $CF_3CH_2CF_3 \rightarrow CF_3CH=CF_2+HF$)

The reactor was heated to 398–423° C. The flow of 1,1,1,3,3,3-hexafluoropropane (6.6 sccm, $1.1 \times 10^{-7}$ m$^3$/s for runs 1, 2 and 3; and 9.7 sccm, $1.6 \times 10^{-7}$ m$^3$/s for runs 4 and 5) and nitrogen was begun to the reactor. The effluent of this reactor which contained 1,1,1,3,3-pentafluoropropene (HFC-1225zc) and HF was passed directly into the next reactor.

| Run No. | T ° C. | $N_2$ sccm |
|---|---|---|
| 1 | 373 | 6.5$^a$ |
| 2 | 398 | 6.5 |
| 3 | 398 | 6.5 |
| 4 | 398 | 6.5 |
| 5 | 398 | 0.7$^b$ |

$^a$equivalent to $1.1 \times 10^{-7}$ m$^3$/s
$^b$equivalent to $1.6 \times 10^{-7}$ m$^3$/s
$^c$equivalent to $1.3 \times 10^{-8}$ m$^3$/s C. Hydrogenation of HFC-1225zc One inch (2.54 cm) Monel™ m nickel alloy compression fittings were used as a reactor (1.91 cm×6.99 cm internal cavity dimensions). This reactor was filled with 0.5% Pd on acid-washed carbon (4.15 g, 8.5 cc). The reactor was heated to 153° C. to 157° C. and the reactor effluent (including both $CF_3CH=CF_2+HF$) from B described above (dehydrofluorination of HFC-236fa) was introduced into the reactor.

| Run No. | CT Sec. | $H_2$ sccm | mole % | | | | % 236fa conv. | % 245fa sel. |
|---|---|---|---|---|---|---|---|---|
| | | | 1225zc | 236fa | 245fa | 254fb | | |
| 1 | 60 | 6.5$^a$ | 3.7 | 71.4 | 24.8 | 0.2 | 28.6 | 86.5 |
| 2 | 60 | 13$^b$ | 2.1 | 71.8 | 25.9 | 0.2 | 28.2 | 91.8 |
| 3 | 60 | 19.5$^c$ | 1.4 | 71.7 | 26.7 | 0.2 | 28.3 | 94.3 |
| 4 | 40 | 82.8$^d$ | 1.4 | 60.0 | 38.4 | 0.2 | 40.0 | 96.1 |
| 5 | 74 | 82.9$^d$ | 1.1 | 67.8 | 30.9 | 0.2 | 32.2 | 95.9 |

$^a$equivalent to $1.1 \times 10^{-7}$ m$^3$/s
$^b$equivalent to $2.2 \times 10^{-7}$ m$^3$/s
$^c$equivalent to $3.2 \times 10^{-7}$ m$^3$/s
$^d$equivalent to $1.4 \times 10^{-6}$ m$^3$/s The contact time shown is the time over the dehydrofluorination catalyst. In this example also, Run 4, when compared to Run 5, shows that even though the contact time is decreased by the addition of about 10 times the amount of nitrogen as used in Run 5, the conversion is increased.

Example 3

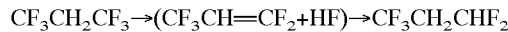

A 15 in (38.1 cm)×⅜ in (0.95 cm) Hastelloy™ nickel alloy tube was filled with 10.4 g (about 13 mL) commercial magnesium oxide, pelletized and ground to 12/20 mesh (1.68/0.84 mm).

A. Catalyst Preparation (1st reactor)

The magnesium oxide precursor was heated to 200° C. for two hours while purging with nitrogen (50 sccm, $8.3 \times 10^{-7}$ m$^3$/s). The nitrogen purge was continued at 50 sccm ($8.3 \times 10^{-7}$ m$^3$/s), while the catalyst was contacted with HF (50 sccm, $8.3 \times 10^{-7}$ m$^3$/s) for 15 minutes. The HF flow was raised to 80 sccm ($1.3 \times 10^{-6}$ m$^3$/s) and the nitrogen flow reduced to 20 sccm ($3.3 \times 10^{-7}$ m$^3$/s) for 25 minutes. The temperature was raised to 250° C. for 75 minutes, 300° C. for 75 minutes, 350° C. for 75 minutes, and 400° C. for 75 minutes while maintaining the flows of HF and nitrogen to provide a fluorided magnesium oxide catalyst.

B. (Reaction: $CF_3CH_2CF_3 \rightarrow CF_3CH=CF_2+HF$)

The reactor was heated to 422° C. The flow of 1,1,1,3,3,3-hexafluoropropane (13.0 sccm, $2.2 \times 10^{-7}$ m$^3$/s) was begun to the reactor. The effluent of this reactor which contained 1,1,1,3,3-pentafluoropropene (HFC-1225zc) and HF was passed directly into the next reactor.

C. Hydrogenation of HFC-1225zc

One inch (2.54 cm) Monel™ nickel alloy compression fittings were used as a reactor (1.91 cm×6.99 cm internal cavity dimensions). This reactor was filled with 0.5% Pd on acid-washed carbon (4.13 g, 8.5 cc). The reactor was heated to 149° C. and the reactor effluent (including both $CF_3CH=CF_2+HF$) from B described above (dehydrofluorination of HFC-236fa) was introduced into the reactor.

| Run No. | CT Sec. | $H_2$ sccm | mole % 1225zc | 236fa | 245fa | 254fb | %236fa conv. | %245fa sel. |
|---|---|---|---|---|---|---|---|---|
| 1 | 60 | 13[a] | 6.4 | 78.4 | 12.2 | 0.1 | 28.2 | 56.4 |

[a]equivalent to $2.2 \times 10^{-7}$ m$^3$/s

The contact time shown is the time over the dehydrofluorination catalyst.

Examples 4–6

$$CF_3CH_2CF_3 \rightarrow CF_3CH=CF_2 + HF$$

General Procedure for the Preparation of Magnesium Fluoride Containing Catalysts Unless stated otherwise, the following general procedure was followed for the preparation of magnesium fluoride containing catalysts containing one or more metal fluorides. An aqueous solution of the metal(s) halide(s) or nitrate(s) in deionized water was treated with 48% aqueous HF with stirring. Stirring was continued overnight and the slurry evaporated to dryness on a steam bath. The dried solid was then calcined in air at 400° C. for about four hours, cooled to room temperature, crushed and sieved to provide a 12–20 mesh (1.68-0.84 mm) fraction which was used in catalyst evaluations.

Catalyst A—MgF$_2$ (commercial sample)
12.0 g of the sieved catalyst in the evaluation.
Catalyst B—MgF$_2$/AlF$_3$ (43:1)
Following the general procedure described above for the preparation of magnesium fluoride containing catalysts, a MgF$_2$/AlF$_3$ catalyst having a nominal magnesium to aluminum atomic ratio of 43:1 was prepared from 251.28 g Mg(NO$_3$)$_2$.6H$_2$O, 7.50 g Al(NO$_3$)$_3$.9H$_2$O and 100 mL 48% aqueous HF. 8.4 g of the sieved catalyst was used in the evaluation.
Catalyst C—MgF$_2$/AlF$_3$ (9:1)
Following the general procedure described above for the preparation of magnesium fluoride containing catalysts, a MgF$_2$/AlF$_3$ catalyst having a nominal magnesium to aluminum atomic ratio of 9:1 was prepared from 237.6 g Mg(NO$_3$)$_2$.6H$_2$O, 34.76 g Al(NO$_3$)$_3$.9H$_2$O and 120 mL 48% aqueous HF. 8.0 g of the sieved catalyst was used in the evaluation.

A 15 in. (38.1 cm)×⅜ in (0.95 cm) Hastelloy™ nickel alloy tube was filled with the amount of catalyst shown above. The reactor was heated to the temperatures recorded in Table 1. The flow of 1,1,1,3,3,3-hexafluoropropane was begun to the reactor with the contact times shown. The dehydrofluorination results (mole %) are shown in Table 1.

TABLE 1

| Ex. | Cat. | T (° C.) | CT | %236fa | %1225zc |
|---|---|---|---|---|---|
| 4 | A | 400 | 120 | 98.9 | .8 |
|   |   | 425 | 120 | 93.7 | 6.1 |
|   |   | 450 | 120 | 89.9 | 9.9 |
|   |   | 475 | 120 | 91.0 | 8.9 |
| 5 | B | 350 | 120 | 91.3 | 8.7 |
|   |   | 400 | 120 | 78.1 | 21.8 |
|   |   | 450 | 120 | 55.1 | 44.7 |
|   |   | 450 | 60 | 47.1 | 52.6 |
|   |   | 450 | 30 | 49.3 | 50.4 |
| 6 | C | 350 | 120 | 91.2 | 8.7 |
|   |   | 400 | 120 | 78.3 | 21.6 |

TABLE 1-continued

| Ex. | Cat. | T (° C.) | CT | %236fa | %1225zc |
|---|---|---|---|---|---|
|   |   | 400 | 60 | 71.5 | 28.4 |
|   |   | 450 | 120 | 54.2 | 45.6 |
|   |   | 450 | 60 | 45.5 | 54.2 |

What is claimed is:

1. A process for producing CF$_3$CH=CF$_2$, comprising: dehydrofluorinating CF$_3$CH$_2$CF$_3$ at an elevated temperature in the vapor phase over a catalyst selected from the group consisting of (1) aluminum fluoride, (2) fluorided alumina, (3) metal supported on a trivalent aluminum compound containing fluoride anion, (4) lanthanum fluoride, (5) fluorided lanthanum oxide, (6) metal supported on a trivalent lanthanum compound containing fluoride anion, (7) trivalent chromium compounds, (8) catalysts of (a) at least one compound selected from the oxides, fluorides and oxyfluorides of magnesium, zinc and mixtures of magnesium and zinc, and optionally (b) at least one compound selected from the oxides, fluorides and oxyfluorides of aluminum, provided that the atomic ratio of aluminum to the total of magnesium and zinc in said catalyst is about 1:4 or less, and mixtures of said catalysts (1) to (8) to produce a product containing CF$_3$CH=CF$_2$ and HF.

2. The process of claim 1 wherein the dehydrofluorination catalyst is a catalyst of (a) at least one compound selected from the oxides, fluorides and oxyfluorides of magnesium, zinc and mixtures of magnesium and zinc, and optionally (b) at least one compound selected from the oxides, fluorides and oxyfluorides of aluminum, provided that the atomic ratio of aluminum to the total of magnesium and zinc in said catalyst is about 1:4, or less.

3. The process of claim 1 wherein the dehydrofluorination is conducted at a temperature in the range of from about 300° C. to about 450° C.

4. The process of claim 1 wherein the dehydrofluorination is run in the presence of an inert gas.

5. The process of claim 1 wherein the dehydrofluorination is run under reduced pressure.

6. The process of claim 1 wherein the dehydrofluorination is run while co-feeding an inert gas and maintaining the total pressure at about atmospheric pressure.

7. The process of claim 1 wherein the dehydrofluorination catalyst is a trivalent chromium compound.

8. The process of claim 1 wherein the dehydrofluorination catalyst is aluminum fluoride or fluorided alumina.

9. The process of claim 1 further comprising isolating CF$_3$CH=CF$_2$ from the dehydrofluorination reaction effluent.

10. The process of claim 9 wherein the CF$_3$CH=CF$_2$ is isolated by distillation.

11. A process for producing CF$_3$CH=CF$_2$, comprising: dehydrofluorinating CF$_3$CH$_2$CF$_3$ in the vapor phase over a catalyst selected from the group consisting of (1) aluminum fluoride, (2) fluorided alumina, (3) metal supported on a trivalent aluminum compound containing fluoride anion, (4) lanthanum fluoride, (5) fluorided lanthanum oxide, (6) metal supported on a trivalent lanthanum compound containing fluoride anion, (7) trivalent chromium compounds, (8) catalysts of (a) at least one compound selected from the oxides, fluorides and oxyfluorides of magnesium, zinc and mixtures of magnesium and zinc, and optionally (b) at least one compound selected from the oxides, fluorides and oxyfluorides of aluminum, provided that the atomic ratio of aluminum to the total of magnesium and zinc in said catalyst is about 1:4 or less, and mixtures of said catalysts (1) to (8), at a pressure less than one atmosphere and a temperature in the range of from about 300° C. to about 450° C., to produce a product containing $CF_3CH=CF_2$ and HF.

12. A process for producing $CF_3CH_2CHF_2$ from $CF_3CH=CF_2$, characterized by:

producing said $CF_3CH=CF_2$ along with HF by dehydrofluorinating $CF_3CH_2CF_3$ at an elevated temperature in the vapor phase over a catalyst selected from the group consisting of (1) aluminum fluoride, (2) fluorided alumina, (3) metal supported on a trivalent aluminum compound containing fluoride anion, (4) lanthanum fluoride, (5) fluorided lanthanum oxide, (6) metal supported on a trivalent lanthanum compound containing fluoride anion, (7) trivalent chromium compounds, (8) catalysts of (a) at least one compound selected from the oxides, fluorides and oxyfluorides of magnesium, zinc and mixtures of magnesium and zinc, and optionally (b) at least one compound selected from the oxides, fluorides and oxyfluorides of aluminum, provided that the atomic ratio of aluminum to the total of magnesium and zinc in said catalyst is about 1:4 or less, and mixtures of said catalysts (1) to (8); and hydrogenating said $CF_3CH=CF_2$ in the vapor phase over a hydrogenation catalyst in the presence of HF and in the presence of nitrogen, helium or argon.

13. The process of claim 12 further comprising isolating $CF_3CH=CF_2$ from the dehydrofluorination reaction effluent by distillation.

14. The process of claim 12 wherein the effluent from the dehydrofluorination is passed with hydrogen over the hydrogenation catalyst.

15. The process of claim 14 wherein the hydrogenation catalyst is a carbon-supported palladium catalyst.

* * * * *